(12) United States Patent
Samproni

(10) Patent No.: US 9,244,085 B2
(45) Date of Patent: Jan. 26, 2016

(54) DEVICES CONTAINING DRIED REAGENTS FOR RECONSTITUTION AS CALIBRATION AND/OR QUALITY CONTROL SOLUTIONS, AND METHODS OF PRODUCTION AND USE THEREOF

(71) Applicant: Siemens Healthcare Diagnostics Inc., Tarrytown, NY (US)

(72) Inventor: Jennifer A. Samproni, Braintree, MA (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 0 days.

(21) Appl. No.: 14/359,799

(22) PCT Filed: Nov. 19, 2012

(86) PCT No.: PCT/US2012/065844
§ 371 (c)(1),
(2) Date: May 21, 2014

(87) PCT Pub. No.: WO2013/078130
PCT Pub. Date: May 30, 2013

(65) Prior Publication Data
US 2014/0308690 A1     Oct. 16, 2014

Related U.S. Application Data

(60) Provisional application No. 61/562,677, filed on Nov. 22, 2011, provisional application No. 61/577,959, filed on Dec. 20, 2011.

(51) Int. Cl.
*G01N 33/96* (2006.01)
*C12N 9/00* (2006.01)
(Continued)

(52) U.S. Cl.
CPC *G01N 33/96* (2013.01); *C12N 9/00* (2013.01); *C12Q 1/26* (2013.01); *C12Q 1/485* (2013.01);
(Continued)

(58) Field of Classification Search
CPC .............. C12N 9/00; C12N 9/96; C12Q 1/26; C12Q 1/485; C12Q 1/54; G01N 33/96; Y10T 436/10; Y10T 436/102499; Y10T 436/204998; Y10T 436/207497; Y10T 436/25; Y10T 436/2525; Y10T 436/2575
USPC ............... 436/8, 11, 68, 79, 66, 84, 133, 136, 436/174, 176, 180; 422/502, 503, 68.1; 435/25, 26, 188, 287.6, 287.9, 14, 15, 435/287.3; 252/408.1; 73/1.01, 1.02, 1.03
See application file for complete search history.

(56) References Cited

U.S. PATENT DOCUMENTS 4,001,142 A * 1/1977 Turner ............................ 436/11
4,141,856 A * 2/1979 Dorwart et al. ................. 436/16
(Continued)

FOREIGN PATENT DOCUMENTS

CN     101122605 A     2/2008
CN     101308150 A     11/2008
(Continued)

OTHER PUBLICATIONS

International Search Report and Written Opinion of International Application No. PCT/US2012/065844 dated Feb. 5, 2013.
(Continued)

*Primary Examiner* — Maureen Wallenhorst
(74) *Attorney, Agent, or Firm* — Kyle D. Petaja

(57) ABSTRACT

Devices contain dried reagents that may be reconstituted and used in the calibration and quality control of sensors. Methods of producing and using the devices are also disclosed.

21 Claims, 2 Drawing Sheets

(51) Int. Cl.
*C12Q 1/26* (2006.01)
*C12Q 1/48* (2006.01)
*C12Q 1/54* (2006.01)
*C12N 9/96* (2006.01)

(52) U.S. Cl.
CPC ... *C12Q 1/54* (2013.01); *C12N 9/96* (2013.01); *Y10T 436/102499* (2015.01); *Y10T 436/204998* (2015.01); *Y10T 436/207497* (2015.01); *Y10T 436/2525* (2015.01); *Y10T 436/2575* (2015.01)

(56) References Cited

U.S. PATENT DOCUMENTS

| | | | |
|---|---|---|---|
| 4,266,941 A * | 5/1981 | Sullivan | 436/68 |
| 4,279,775 A * | 7/1981 | Louderback et al. | 436/11 |
| 4,289,648 A * | 9/1981 | Hoskins et al. | 436/11 |
| 4,469,792 A * | 9/1984 | Simmonds et al. | 436/11 |
| 4,485,086 A * | 11/1984 | Wong | 424/1.65 |
| 4,960,708 A * | 10/1990 | Zowtiak et al. | 436/11 |
| 5,204,266 A * | 4/1993 | Calzi | 436/11 |
| 5,776,563 A | 7/1998 | Buhl et al. | |
| 5,854,210 A * | 12/1998 | Burhop et al. | 514/15.3 |
| 6,551,842 B1 | 4/2003 | Carpenter | |
| 2001/0039059 A1 | 11/2001 | Freitag et al. | |
| 2002/0011408 A1 | 1/2002 | Lee et al. | |
| 2006/0046301 A1 | 3/2006 | Happe | |
| 2006/0068399 A1 | 3/2006 | McMillan et al. | |
| 2008/0014114 A1 | 1/2008 | Van Atta et al. | |
| 2008/0269314 A1 * | 10/2008 | Debetten-Court et al. | 514/423 |
| 2009/0142771 A1 * | 6/2009 | Breidenthal et al. | 435/6 |

FOREIGN PATENT DOCUMENTS

| | | |
|---|---|---|
| CN | 101893639 A | 11/2010 |
| CN | 102089664 A | 6/2011 |
| WO | 9602828 A1 | 2/1996 |
| WO | 2007029159 A1 | 3/2007 |

OTHER PUBLICATIONS

Schembri et al., "Portable simultaneous multiple analyte whole-blood analyzer for point-of-care testing", Clinical Chemistry, Sep. 1992; vol. 38, No. 9, pp. 1665-1670.

Papadea et al., "Evaluation of the i-STAT Portable Clinical Analyzer for point-of-care blood testing in the intensive care units of a university children's hospital", Annals of Clinical & Laboratory Science, 2002; vol. 32, No. 3, pp. 231-243.

Noonan et al., "Long-term reproducibility of a new pH/blood-gas quality-control system compared to two other procedures", Clinical Chemistry, Nov. 1976; vol. 22, No. 11, pp. 1817-1820.

* cited by examiner

US 9,244,085 B2

DEVICES CONTAINING DRIED REAGENTS FOR RECONSTITUTION AS CALIBRATION AND/OR QUALITY CONTROL SOLUTIONS, AND METHODS OF PRODUCTION AND USE THEREOF

CROSS REFERENCE TO RELATED APPLICATIONS

This application claims benefit under 35 U.S.C. 119(e) of U.S. Ser. No. 61/562,677, filed Nov. 22, 2011 and of U.S. Ser. No. 61/577,959 filed Dec. 20, 2011. The entire contents of the above-referenced applications are expressly incorporated herein by reference.

STATEMENT REGARDING FEDERALLY SPONSORED RESEARCH OR DEVELOPMENT

Not Applicable.

BACKGROUND OF THE INVENTION

1. Field of the Inventive Concept(s)

The presently disclosed and claimed inventive concept(s) relates generally to reagents used as calibration and/or quality control solutions for sensors, and in particular, but not by way of limitation, to a microfluidics device containing dried reagents for reconstitution as calibration and/or quality control solutions, and methods of producing and using same.

2. Description of the Background Art

Liquid solutions are currently used in the calibration and quality control of sensors. For liquid reagents with pre-determined gas concentrations, such as for oxygen and carbon dioxide, these liquid reagents are typically stored in glass ampoules or laminate barrier pouches, where the barrier material serves to maintain a pre-determined amount of dissolved gas in the solution. However, the shelf life of these solutions may be limited as a result of degradation products or cross-reaction products.

Therefore, there is a need in the art for new and improved reagent embodiments and delivery systems for use in the calibration and quality control of sensors. It is to devices containing said compositions, as well as methods of producing and using same, that the presently disclosed and claimed inventive concept(s) is directed.

DETAILED DESCRIPTION OF THE INVENTIVE CONCEPT(S)

Figure 1:
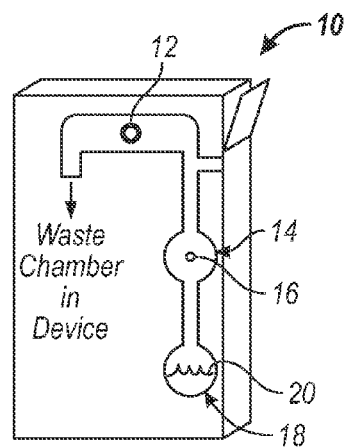
FIG. 1 is a perspective view of an embodiment of a microfluidics device constructed in accordance with the presently disclosed and claimed inventive concept(s).

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses and chemical analyses.

All patents, published patent applications and non-patent publications mentioned in the specification are indicative of the level of skill of those skilled in the art to which this presently disclosed and claimed inventive concept(s) pertains. All patents, published patent applications and non-patent publications referenced in any portion of this application are herein expressly incorporated by reference in their entirety to the same extent as if each individual patent or publication was specifically and individually indicated to be incorporated by reference.

All of the articles, compositions and/or methods disclosed and claimed herein can be made and executed without undue experimentation in light of the present disclosure. While the articles, compositions and methods of the inventive concept(s) have been described in terms of preferred embodiments, it will be apparent to those of skill in the art that variations may be applied to the articles, compositions and/or methods and in the steps or in the sequence of steps of the methods described herein without departing from the concept, spirit and scope of the inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

The term "about" is used to indicate that a value includes the inherent variation of error for the device, the method being employed to determine the value and/or the variation that exists among study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Turning now to the presently disclosed and claimed inventive concept(s), a composition comprising a predetermined amount of at least one lyophilized reagent is provided. The predetermined amount of lyophilized reagent comprises at least one of a salt, a protein, and a catalyst. The lyophilized reagent may be reconstituted with an excipient in situ to provide a single unit of calibration and/or quality control solution for monitoring the performance of blood gas, electrolyte and/or metabolite instrumentation. The lyophilized reagent may be disposed in any form, such as but not limited to, a bead or a hemisphere. The composition may be maintained in a substantially air tight environment until use thereof.

In certain embodiments, the predetermined amount of lyophilized reagent may include salt(s), protein(s) and/or catalyst(s). Examples of compositions that may be present in the lyophilized reagent utilized in accordance with the presently disclosed and claimed inventive concept(s) include, but are not limited to, sodium, potassium, calcium, and/or chlorine salts (such as but not limited to, calcium chloride, lithium chloride, sodium bicarbonate, sodium citrate, sodium sulfite, and/or sodium sulfate), glucose oxidase, glucose dehydrogenase, hexokinase, glucose dehydrogenase, hexokinase, lactate oxidase, hemoglobin, cobalt, and combinations thereof. Examples of reconstituted calibration and/or quality control solutions utilized in accordance with the presently disclosed and claimed inventive concept(s) include, but are not limited to, analytes, metabolites and/or gases.

The presently disclosed and claimed inventive concept(s) also includes devices for monitoring the performance of blood gas, electrolyte and/or metabolite instrumentation and that include at least one lyophilized reagent for reconstitution and use in situ as a calibration and/or quality control solution for contacting a sensor are disclosed. In one embodiment, the device contains at least two cavities. The first cavity has a predetermined amount of at least one lyophilized reagent (as described herein above) disposed therein. The second cavity is an activatable cavity, and said cavity is in fluidic communication with the cavity having lyophilized reagent disposed therein upon activation thereof. The activatable cavity has a predetermined amount of excipient disposed therein, wherein upon activation of the activatable cavity, the excipient moves from the activatable cavity into the cavity having the lyophilized reagent disposed therein, whereby the excipient reconstitutes the lyophilized reagent in situ to provide at least one calibration and/or quality control solution.

The device may further include a sensor, wherein the first cavity is in fluidic communication with the sensor. The sensor may be any sensor useful with blood gas, electrolyte and/or metabolite instrumentation. Said sensors are well known in the art, and therefore no further discussion thereof is deemed necessary.

The reconstituted calibration and/or quality control solution(s) may include analyte(s), metabolite(s) and/or gas(es). A single cavity of the device may contain multiple lyophilized reagents for reconstitution as multiple calibration and/or quality control solutions.

In construction of the device, at least a portion of the device may be sealed to maintain the lyophilized reagent in a substantially air tight environment until use thereof; this prevents exposure of the lyophilized reagent to humidity that could collapse the bead/hemisphere and interfere with reconstitution thereof. The lyophilized reagent may be disposed in the cavity by any method known in the art; for example but not by way of limitation, the lyophilized reagent may be sprayed into wells and/or disposed in the form of bead(s)/hemisphere(s) in metering cavities. In certain embodiments, the forms/beads of lyophilized reagent may contain a plurality of lyophilized reagents; in this manner, multiple analytes can be produced simultaneously.

The activatable cavity may be activated by any method known in the art or otherwise contemplated herein; for example, but not by way of limitation, the activatable cavity may be in the form of a blister pack and/or barrier pouch, and the disposal of pressure thereon results in depression thereof, followed by flow of the excipient therefrom and into the cavity containing the lyophilized reagent.

The plurality of lyophilized reagents may be reconstituted with a single excipient or multiple excipients. Each of these excipients may be in any form that allows said excipient to function in accordance with the presently disclosed and claimed inventive concept(s). For example but not by way of limitation, the excipient(s) may be in the form of a liquid or a gel. Any excipient known in the art and capable of use as described herein (i.e., capable of imparting hydrophilicity to a dried bead/hemisphere of reagent) is encompassed within the scope of the presently disclosed and claimed inventive concept(s). When multiple excipients are utilized, they may be disposed in the same activatable cavity or in separate activatable cavities.

The flow of excipient from the activatable cavity and the flow of reconstituted reagent from the cavity into contact with the sensor may occur by any mechanisms known in the art or otherwise contemplated herein. For example but not by way of limitation, capillary force may move the excipient/reconstituted reagent through the device. Alternatively, pressure or vacuum may be utilized therewith.

In certain embodiments, a desired gas reagent may be generated in situ. One particular non-limiting example of a system of the presently disclosed and claimed inventive concept(s) includes a lyophilized reagent that includes sodium bicarbonate and is redissolved in an excipient of a low pH matrix; the resultant reconstituted calibration and/or quality control solution comprises carbon dioxide. In another particular non-limiting example, the lyophilized reagent comprises an oxygen scavenger (such as, but not limited to, sodium sulfate), the excipient comprises water, and the reconstituted calibration and/or quality control solution comprises negligible oxygen. In this manner, solutions containing various analyte or gas concentrations are generated in situ from a single liquid reagent (i.e., pure water). As the liquid from a single source passes through microchannels containing the dried reagent bead(s)/hemisphere(s), the concentrated analyte and/or metabolite is redissolved and/or the gas is altered using either gas generating reactions or gas scavenging reactions.

In certain embodiments, the device may further include a second cavity having a predetermined amount of at least one second lyophilized reagent (as described herein above) disposed therein. The predetermined amount of second lyophilized reagent is in fluidic communication with the single activatable cavity having a predetermined amount of excipient disposed therein (and which is also in fluidic communication (upon activation thereof) with the first cavity containing lyophilized reagent). Upon activation of the activatable cavity, the excipient moves from the activatable cavity into the first and second cavities, each containing lyophilized reagent; in this manner, the excipient reconstitutes the first and second lyophilized reagents in situ to provide at least two calibration and/or quality control solutions. The first and second lyophilized reagents may be the same or different.

Alternatively, the device containing two cavities with lyophilized reagents disposed therein may also be provided with two activatable cavities, each in fluidic communication with a cavity containing lyophilized reagent (following activation thereof), and each having a predetermined amount of excipient disposed therein (wherein the excipients present in the two activatable cavities may be the same or different). In the same manner as described herein above for activation of the first activatable cavity, the excipient moves from the second activatable cavity upon activation thereof into the second cavity having the second lyophilized reagent disposed therein, whereby the excipient reconstitutes the second lyophilized reagent in situ to provide a second calibration and/or quality control solution. When the device includes a sensor, the two cavities may both be in fluidic communication with the sensor, whereby the reconstituted reagents produced in the first and second cavities pass over the sensor.

In yet another alternative, the device may contain more than two cavities with lyophilized reagents disposed therein (as described in detail herein above). These three or more cavities may each be in fluidic communication with their own activatable cavity containing excipient (upon activation of said activatable cavity), or two or more of these cavities may share a single activatable cavity that contains a predetermined amount of excipient sufficient to reconstitute the lyophilized reagents present in the two or more cavities.

In addition, when the device contains two or more sets of cavities (whether they share an activatable cavity or are each connected to separate activatable cavities), the lyophilized reagents may be reconstituted simultaneously or in a staggered manner.

The presently disclosed and claimed inventive concept(s) is also directed to a method for monitoring the performance of blood gas, electrolyte and/or metabolite instrumentation. In the method, any of the devices described herein above are disposed into at least one of a blood gas, electrolyte and metabolite instrument, and the device is activated for calibration and/or quality control of the blood gas, electrolyte and/or metabolite instrument.

Turning now to the Drawings, FIG. 1 depicts a device 10 for use in accordance with the presently disclosed and claimed inventive concept(s). The device 10 is utilized in monitoring the performance of blood gas, electrolyte and/or metabolite instrumentation. The device 10 may be any type of disposable cartridge (for example but not by way of limitation, a laminate card or a molded card) known in the art or otherwise described herein, and capable of containing a microfluidic structure as described in detail herein below. The device 10 contains a sensor 12 and elements for producing one or more solution(s) for calibration and/or quality control. These elements include at least one cavity 14 in fluidic communication with the sensor 12. The cavity 14 contains at least one lyophilized reagent 16 (the lyophilized reagent depicts as being in bead/hemisphere form). The cavity 14 is also in fluidic communication with an activatable cavity 18 containing an excipient 20 (such as but not limited to, a liquid or a gel) for reconstitution of the lyophilized reagent 16 (wherein the fluidic communication is provided upon activation of the activatable cavity 18). The activatable cavity 18 may be, for example but not by way of limitation, a blister pack or other type of sealed cavity that is sealed to prevent contact between the excipient 20 and the lyophilized reagent 16 until use of the device 10. In use, the activatable cavity 18 may be activated such as (but not by way of limitation) by depression thereof, thus pushing the excipient 20 into the cavity 14 containing the lyophilized reagent 16 to reconstitute the lyophilized reagent 16, thereby providing a reconstituted calibration and/or quality control solution. The reconstituted calibration and/or quality control solution is then brought into contact with the sensor 12. The resultant reconstituted calibration and/or quality control solution will contain a known quantity of ions, proteins and/or gases that will serve as calibrators and/or control solutions for the sensor of interest.

In certain embodiments, some mixing may occur in the cavity 14 between the lyophilized reagent 16 and the excipient 20 to ensure complete reconstitution of the lyophilized reagent 16 and to ensure homogeneity of the resultant reconstituted calibration and/or quality control solution. Any method of mixing known in the microfluidics art or otherwise contemplated herein may be utilized in accordance with the presently disclosed and claimed inventive concept(s). In addition, the flow of the excipient 20 into the cavity 14 may be controlled by any method known in the art or otherwise contemplated herein; for example, but not by way of limitation, the force of activating (i.e., depressing) the activatable cavity 18 may provide the necessary force to push the desired amount of excipient 20 into the cavity 14. Likewise, the flow of the reconstituted calibration and/or quality control solution (whether in the form of ion(s), protein(s) and/or gas(es)) from the cavity 14 and over the sensor 12 may be controlled by any method known in the art or otherwise contemplated herein; for example but not by way of limitation, the force of activating (i.e., depressing) the activatable cavity 18 may ultimately provide the necessary force to push the reconstituted calibration and/or quality control solution out of the cavity 14 and over the sensor 12.

Figure 2:
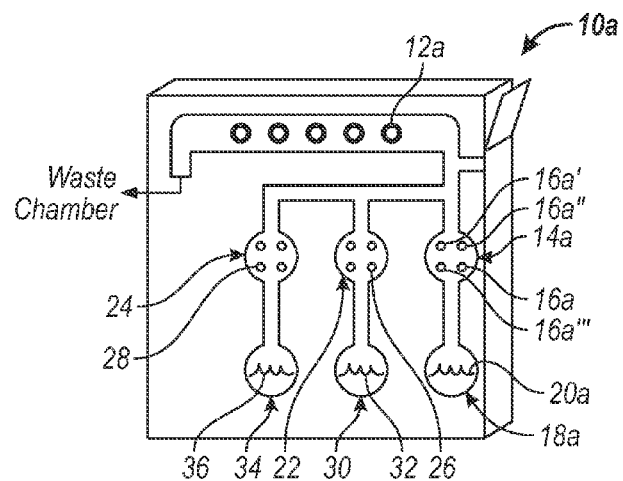
FIG. 2 is a perspective view of another embodiment of a microfluidics device constructed in accordance with the presently disclosed and claimed inventive concept(s).

FIG. 2 depicts a device 10a, another embodiment of a microfluidics device utilized in monitoring the performance of blood gas, electrolyte and/or metabolite instrumentation and constructed in accordance with the presently disclosed and claimed inventive concept(s). The device 10a is similar to the device 10 of FIG. 1, except that the device 10a contains multiple cavities with multiple beads/hemispheres of lyophilized reagents, each in contact with a different activatable cavity containing excipient. The device 10 contains a sensor array 12a in fluidic communication with three cavities containing lyophilized reagents: a first cavity 14a, a second cavity 22 and a third cavity 24. The first cavity 14a contains four beads/hemispheres 16a, 16a', 16a" and 16a'" of lyophilized reagent(s). The four beads/hemispheres 16a, 16a', 16a" and 16a'" may contain the same reagent or different reagents. The second cavity 22 contains a plurality of beads/hemispheres of lyophilized reagent(s) (singularly represented by the reference numeral 26), while the third cavity 24 contains a plurality of beads/hemispheres of lyophilized reagent(s) (singularly represented by the reference numeral 28); the plurality of beads/hemispheres 26 may contain the same reagent or different reagents, whereas the plurality of beads/hemispheres 28 may contain the same reagent or different reagents.

The cavity 14a is in fluidic communication with an activatable cavity 18a containing an excipient 20a (wherein the fluidic communication is provided upon activation of the activatable cavity 18a). The cavity 22 is in fluidic communication with an activatable cavity 30 containing an excipient 32 (wherein the fluidic communication is provided upon activation of the activatable cavity 30). The cavity 24 is in fluidic communication with an activatable cavity 34 containing an excipient 36 (wherein the fluidic communication is provided upon activation of the activatable cavity 34). The excipients 20a, 32 and 36 may be the same or different. The activatable cavities 18a/30/34 containing the excipients 20a/32/36 function in the same manner as described herein above for the activatable cavity 18 containing the excipient 20, and thereby reconstitute the beads/hemispheres 16-16'"/26/28 of lyophilized reagent(s). In this manner, resultant reconstituted calibration and/or quality control solution(s) containing a known quantity of ions, proteins and/or gases are provided that will serve as calibrators and/or control solutions for the sensor array 12a. It will be understood that the activatable cavities 18a, 30 and 34 may be activated at the same time (simultaneously), or the activation of the activatable cavities 18a, 30 and 34 may be staggered.

Figure 3:
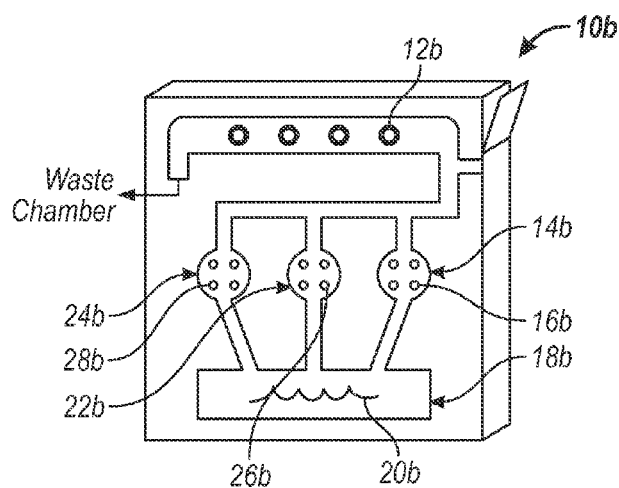
FIG. 3 is a perspective view of yet another embodiment of a microfluidics device constructed in accordance with the presently disclosed and claimed inventive concept(s).

FIG. 3 depicts yet another embodiment of the presently disclosed and claimed inventive concept(s). A device 10b shown in FIG. 3 is similar to the device 10a shown in FIG. 2, except that the three cavities (14b, 22b and 24b) containing beads/hemispheres of lyophilized reagent (the plurality of beads/hemispheres represented singularly in each cavity 14b, 22b and 24b by the reference numerals 16b, 26b and 28b, respectively) are in fluidic communication with a single activatable cavity 18b containing excipient 20b (upon activation of the activatable cavity 18b) for reconstitution of all of the beads/hemispheres represented by reference numerals 16b, 26b and 28b. The device 10b functions in the same manner as the devices 10 and 10a following reconstitution of the calibration and/or quality control solution(s).

Figure 4:
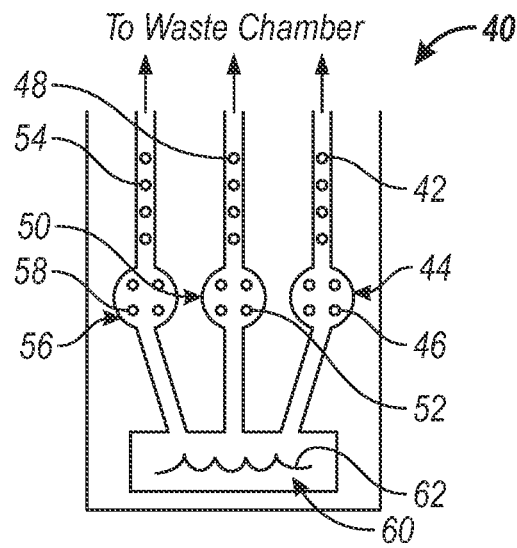
FIG. 4 is a perspective view of a further embodiment of a microfluidics device constructed in accordance with the presently disclosed and claimed inventive concept(s).
Figure 5:
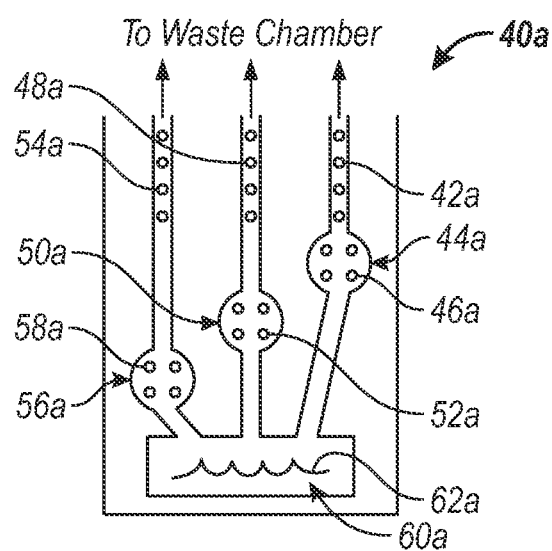
FIG. 5 is a perspective view of a yet further embodiment of a microfluidics device constructed in accordance with the presently disclosed and claimed inventive concept(s).

In the embodiments shown in FIGS. 2-3, the multiple reconstituted calibration and/or quality control solutions have a common sensor path. FIGS. 4-5 depict devices 40 and 40a utilized in monitoring the performance of blood gas, electrolyte and/or metabolite instrumentation, wherein the devices 40 and 40a function in a similar manner as the devices 10, 10a and 10b of FIGS. 1-3, except that the devices 40 and 40a contain multiple sensor arrays.

FIG. 4 depicts a device 40 that include a first sensor array 42 in fluidic communication with a first cavity 44 containing one or a plurality of beads/hemispheres of lyophilized reagent 46. The device 40 also includes a second sensor array 48 in fluidic communication with a second cavity 50 containing one or a plurality of beads/hemispheres of lyophilized reagent 52. The device 40 further contains a third sensor array 54 in fluidic communication with a third cavity 56 containing one or a plurality of beads/hemispheres of lyophilized reagent 58. The three cavities 44, 50 and 56 containing beads/hemispheres of lyophilized reagent(s) 46, 52 and 58, respectively, are in fluidic communication with a single activatable cavity 60 containing excipient 62 for reconstitution of all of the beads/hemispheres represented by reference numerals 46, 52 and 58 (wherein the fluidic communication is provided upon activation of the activatable cavity 60).

FIG. 5 depicts a device 40a that include a first sensor array 42a in fluidic communication with a first cavity 44a containing one or a plurality of beads/hemispheres of lyophilized reagent 46a. The device 40a also includes a second sensor array 48a in fluidic communication with a second cavity 50a containing one or a plurality of beads/hemispheres of lyophilized reagent 52a. The device 40a further contains a third sensor array 54a in fluidic communication with a third cavity 56a containing one or a plurality of beads/hemispheres of lyophilized reagent 58a. The three cavities 44a, 50a and 56a containing beads/hemispheres of lyophilized reagent(s) 46a, 52a and 58a, respectively, are in fluidic communication with a single activatable cavity 60a containing excipient 62a for reconstitution of all of the beads/hemispheres represented by reference numerals 46a, 52a and 58a (wherein the fluidic communication is provided upon activation of the activatable cavity 60a).

The devices 40 and 40a of FIGS. 4-5 differ from one another in that the device 40 provides simultaneous reconstitution of the beads/hemispheres of lyophilized reagents 46, 52 and 58, while the device 40a provides staggered reconstitution of the beads/hemispheres of lyophilized reagents 46a, 52a and 58a. The sensors 42, 48 and 54 of the device 40 of FIG. 4 and the sensors 42a, 48a and 54a of the device 40a of FIG. 5 are depicted as being in line with one another; however, it is to be understood that one or more of the sensors 42/42a, 48/48a and 54/54a may be staggered with relation to one another. In addition, when the sensors 42/42a, 48/48a and 54/54a are positioned in line with one another, two or more of the sensors 42/42a, 48/48a and 54/54a may be redundant.

While FIGS. 4-5 depict the use of a single activatable cavity 60/60a containing a single excipient 62/62a, it is to be understood that two or more of the cavities 44/44a, 50/50a and 56/56a may each be supplied by different activatable cavities containing the same or different excipients, in a similar manner as to that described for the device 10a of FIG. 2.

The number of beads/hemispheres of lyophilized reagent present in each of the cavities depicted in FIGS. 1-5 are for purposes of illustration only and are not to be construed as limiting. Moreover, it is to be understood that any of the cavities described and claimed herein may be provided with only one bead/hemisphere of lyophilized reagent disposed therein.

EXAMPLES

Examples are provided hereinbelow. However, the present invention is to be understood to not be limited in its application to the specific experimentation, results and laboratory procedures. Rather, the Examples are simply provided as one of various embodiments and are meant to be exemplary, not exhaustive.

Example 1

The present Example provides an outline of the preparation, lyophilization and reconstitution of point of care blood gas (POC BG), electrolyte and metabolite reagents. In this Example, a lyophilized bead/hemisphere of calibration solution was prepared for use in future point of care products.

First, a concentrate of a calibration solution was prepared using the 5× concentrate values shown in Table 1.

TABLE 1

| Cal Solution 5x Concentrate | | | | |
|---|---|---|---|---|
| component | MW | MMOL/L | G/L | 5x |
| DI WATER | | liters | 993.8 | |
| MOPS | 209.30 | 40.0 | 8.3720 | 41.860 |
| NaOH pellets | 40.0 | 24.0 | 0.9600 | 4.800 |
| Glucose | 180.16 | 10.1 | 1.8196 | 9.098 |
| NaCl | 58.44 | 89.2 | 5.2128 | 26.064 |
| Citric acid*$H_2O$ | 210.1 | 1.7 | 0.3572 | 1.786 |
| $NaHCO_3$** | 84.01 | 5.8 | 0.4873 | 2.436 |
| KCl | 74.56 | 4.0 | 0.2982 | 1.491 |
| $CaCl_2$*$2H_2O$ | 147.02 | 2.32 | 0.341 | 1.705 |
| Li Lactate | 96.01 | 2.0 | 0.1920 | 0.960 |

In addition to the reagents listed in Table 1, protectants and stabilizers may be included to help produce a more viable product. The protectant(s) and/or stabilizer(s) are generally used singly or in combination in concentrations from about 1% to about 30%. The protectant(s) and/or stabilizer(s) provide: (1) stability to the reagent formulation components; (2) a stable and viable lyophilization 'cake' that is easy to handle and easy to reconstitute; and (3) provide structure to the 'cake'. Typically, the protectants/stabilizers include, for example but not by way of limitation, polyhydroxy compounds such as, but not limited to, sugars (mono-, di-, and polysaccharides), polyalcohols, and their derivatives, as well as other compounds such as but not limited to, PEGs, PVP, carboxymethylcellulose, trehalose, sucrose, maltodextrins, Ficoll 70, PVP 40, PEG 8000, BSA and the like. Regardless of the compound(s) used, the protectants/stabilizers must not interfere with the formulation (stability) or with the sensors or the instrument.

For the fill volume utilized in lyophilization: This is a 5× concentrate, so fill and reconstitution volume should match. For example—fill 40 µl and add 200 µl of the diluent to reconstitute. Volume will depend on sample size needed in the device.

The container used should be compatible with the reagent and not leach anything that would harm the reagent, sensor or instrument. It must be capable of being frozen and heated without being affected or affecting the reagent. A non-limiting example of a container that may be utilized in accordance with the presently disclosed and claimed inventive concept(s) is a 96 well plate.

The procedure for lyophilization begins by filling the 96 well plates (or other container) with a chosen volume. The plates are then frozen rapidly (such as but not by limitation, by immersion in liquid $N_2$ or another super cooling solution (e.g. methanol/dry ice)). The rate of freezing is affected by various factors (such as but not limited to, the reagent composition and ionic strength); the freezing rate must be fast, but not so fast as to cause large ice crystals and thus ensure that most of the water is frozen. The freezing cycle can affect the turbidity and homogeneity of the reconstituted reagent. Depending on the lyophilizer, the plates may be frozen directly on the shelves; however, this would require very good contact and conductivity between the plate and shelf to be efficient. The reagent is generally frozen to a temperature below about −50 to about −80° C. The temperature is defined by determining the eutectic point.

There are several possible lyophilization programs and steps to use; however, the process should generally include the following steps:
  (a) A primary drying step is utilized for removal of ice. This step is performed partial vacuum and with moderate heat (generally kept <0° C.) applied to the shelf. The object is to cause sublimation without causing structure collapse. This step may be performed at steady temperature or under conditions of a heat gradient where the temperature is gradually raised. This process is typically slow and is volume dependent.
  (b) A secondary drying step is utilized for removal of unfrozen water. This step is performed under a higher vacuum and with increased temperature applied to the shelf. This step is time dependent on the conditions and concentrations utilized; this step is determined by the moisture content required for stability (generally <1% especially if glucose is present).
  (c) In the end of cycle step, the temperature is brought to room temperature or slightly there below. The vacuum is replaced with dry inert gas. The samples are capped (this step may be performed manually or automatically with a bladder system & special caps). The product is then stored in sealed laminate or other moisture tight container.

The lyophilized bead/hemisphere is subsequently reconstituted as described above (i.e., diluted 1:5 with diluent).

Example 2

Calibrator or control solutions containing salts such as but not limited to, calcium chloride, lithium chloride, sodium bicarbonate, etc., and/or proteins such as glucose oxidase, glucose dehydrogenase, hexokinase, lactate oxidase, etc., in known concentrations are lyophilized. Upon reconstitution with deionized water, a known concentration of each ion or protein is produced.

To create specific carbon dioxide gas concentrations, the lyophilized reagent disposed cavity of the device of the presently disclosed and claimed inventive concept(s) contains sodium bicarbonate, which is reconstituted with an excipient that includes a pH modifier such as sodium citrate; in this manner, carbon dioxide is generated.

Low oxygen gas solutions are created by incorporating an oxygen scavenger such as sodium sulfite, and optionally a catalyst such as cobalt, into the lyophilized reagent disposed in the device of the presently disclosed and claimed inventive concept(s).

Any of the lyophilized beads/hemispheres described herein above are redissolved in a known concentration of liquid/gel, and the resulting solution is used to serve as a calibrator or control for any of the ions incorporated into the lyophilized bead (i.e., pH sensor, sodium sensor, lactate sensor, etc.).

Additionally, beads/hemispheres with different known concentrations of analytes are disposed in different wells/cavities of the disposable device, and a single water source is used as the excipient (present in the single activatable cavity) to concurrently generate multiple calibration/control solutions in situ.

Thus, in accordance with the present invention, there have been provided compositions and devices, as well as methods of producing and using same, which fully satisfy the objectives and advantages set forth hereinabove. Although the invention has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

The invention claimed is:

1. A device for monitoring the performance of blood gas, electrolyte and/or metabolite instrumentation, comprising:
   at least one cavity having a predetermined amount of at least one lyophilized reagent disposed therein, wherein the predetermined amount of lyophilized reagent comprises at least one of a salt, a protein, and a catalyst, the at least one cavity including a first cavity;
   at least one activatable cavity in fluidic communication with the at least one cavity having lyophilized reagent disposed therein, the at least one activatable cavity having a predetermined amount of excipient disposed therein, wherein upon activation of the activatable cavity, the excipient moves from the at least one activatable cavity into the at least one cavity having lyophilized reagent disposed therein whereby the excipient reconstitutes the lyophilized reagent in situ to provide at least one calibration and/or quality control solution;
   wherein at least a portion of the device is sealed to maintain the lyophilized reagent in a substantially air tight environment until use thereof; and
   wherein the lyophilized reagent comprises sodium bicarbonate, the excipient comprises low pH matrix, and the reconstituted calibration and/or quality control solution comprises carbon dioxide.

2. The device of claim 1, wherein the lyophilized reagent further comprises at least one of calcium chloride, lithium chloride, sodium citrate, sodium sulfite, sodium sulfate, glucose oxidase, glucose dehydrogenase, hexokinase, glucose dehydrogenase, lactate oxidase, hemoglobin, cobalt, and combinations thereof.

3. The device of claim 1, wherein the reconstituted calibration and/or quality control solution comprises an analyte, a metabolite and/or a gas.

4. The device of claim 1, wherein the lyophilized reagent is disposed in the cavity in the form of a bead or hemisphere.

5. The device of claim 1, further comprising a sensor in fluidic communication with the at least one cavity.

6. The device of claim 1, further comprising a second cavity having a predetermined amount of at least one second lyophilized reagent disposed therein, wherein the predetermined amount of second lyophilized reagent comprises at least one of a salt, a protein, and a catalyst, and wherein the predetermined amount of second lyophilized reagent is in fluidic communication with the at least one activatable cavity having a predetermined amount of excipient disposed therein, wherein upon activation of the activatable cavity, the excipient moves from the at least one activatable cavity into the second cavity having the second lyophilized reagent disposed therein whereby the excipient reconstitutes the second lyophilized reagent in situ to provide at least one calibration and/or quality control solution.

7. The device of claim 6, wherein the lyophilized reagents present in the first and second cavities are the same.

8. The device of claim 6, wherein the lyophilized reagents present in the first and second cavities are different.

9. The device of claim 6, further comprising a sensor in fluidic communication with the first and second cavities.

10. A method for monitoring the performance of blood gas, electrolyte and/or metabolite instrumentation, the method comprising the steps of:
    disposing the device of claim 8 into at least one of a blood gas, electrolyte and metabolite instrument; and
    activating the device of claim 8 for calibration and/or quality control of the blood gas, electrolyte and/or metabolite instrument, wherein upon activating the device of claim 1, the excipient moves from the at least one activatable cavity into the at least one cavity having lyophilized reagent disposed therein whereby the excipient reconstitutes the lyophilized reagent in situ to provide at least one calibration and/or quality control solution.

11. A device for monitoring the performance of blood gas, electrolyte and/or metabolite instrumentation, comprising:
    at least one cavity having a predetermined amount of at least one lyophilized reagent disposed therein, wherein the predetermined amount of lyophilized reagent comprises at least one of a salt, a protein, and a catalyst, the at least one cavity including a first cavity;
    at least one activatable cavity in fluidic communication with the at least one cavity having lyophilized reagent disposed therein, the at least one activatable cavity having a predetermined amount of excipient disposed therein, wherein upon activation of the activatable cavity, the excipient moves from the at least one activatable cavity into the at least one cavity having lyophilized reagent disposed therein whereby the excipient reconstitutes the lyophilized reagent in situ to provide at least one calibration and/or quality control solution;
    wherein at least a portion of the device is sealed to maintain the lyophilized reagent in a substantially air tight environment until use thereof; and
    wherein the lyophilized reagent comprises an oxygen scavenger, the excipient comprises water, and the reconstituted calibration and/or quality control solution comprises negligible oxygen.

12. The device of claim 11, wherein the lyophilized reagent comprises at least one of calcium chloride, lithium chloride, sodium bicarbonate, sodium citrate, sodium sulfite, sodium sulfate, glucose oxidase, glucose dehydrogenase, hexokinase, glucose dehydrogenase, hexokinase, lactate oxidase, hemoglobin, cobalt, and combinations thereof.

13. The device of claim 11, wherein the reconstituted calibration and/or quality control solution comprises an analyte, a metabolite and/or a gas.

14. The device of claim 11, wherein the lyophilized reagent is disposed in the cavity in the form of a bead or hemisphere.

15. The device of claim 11, further comprising a sensor in fluidic communication with the at least one cavity.

16. The device of claim 11, further comprising a second cavity having a predetermined amount of at least one second lyophilized reagent disposed therein, wherein the predetermined amount of second lyophilized reagent comprises at least one of a salt, a protein, and a catalyst, and wherein the predetermined amount of second lyophilized reagent is in fluidic communication with the at least one activatable cavity having a predetermined amount of excipient disposed therein, wherein upon activation of the activatable cavity, the excipient moves from the at least one activatable cavity into the second cavity having the second lyophilized reagent disposed therein whereby the excipient reconstitutes the second lyophilized reagent in situ to provide at least one calibration and/or quality control solution.

17. The device of claim 16, wherein the lyophilized reagents present in the first and second cavities are the same.

18. The device of claim 16, wherein the lyophilized reagents present in the first and second cavities are different.

19. The device of claim 16, further comprising a sensor in fluidic communication with the first and second cavities.

20. A method for monitoring the performance of blood gas, electrolyte and/or metabolite instrumentation, the method comprising the steps of:
- disposing the device of claim 11 into at least one of a blood gas, electrolyte and metabolite instrument; and
- activating the device of claim 11 for calibration and/or quality control of the blood gas, electrolyte and/or metabolite instrument, wherein upon activating the device of claim 11, the excipient moves from the at least one activatable cavity into the at least one cavity having lyophilized reagent disposed therein whereby the excipient reconstitutes the lyophilized reagent in situ to provide at least one calibration and/or quality control solution.

21. A method for monitoring the performance of blood gas, electrolyte and/or metabolite instrumentation, the method comprising the steps of:
- disposing a device for monitoring the performance of blood gas, electrolyte and/or metabolite instrument into at least one of a blood gas, electrolyte and metabolite instrument; and
- activating the device for calibration and/or quality control of the blood gas, electrolyte and/or metabolite instrument, wherein the device comprises:
- at least one cavity having a predetermined amount of at least one lyophilized reagent disposed therein, wherein the predetermined amount of lyophilized reagent comprises at least one of a salt, a protein, and a catalyst; and
- at least one activatable cavity in fluidic communication with the at least one cavity having lyophilized reagent disposed therein, the at least one activatable cavity having a predetermined amount of excipient disposed therein, wherein upon activation of the activatable cavity, the excipient moves from the at least one activatable cavity into the at least one cavity having lyophilized reagent disposed therein whereby the excipient reconstitutes the lyophilized reagent in situ to provide at least one calibration and/or quality control solution;

wherein at least a portion of the device is sealed to maintain the lyophilized reagent in a substantially air tight environment until use thereof, wherein upon activating the device, the excipient moves from the at least one activatable cavity into the at least one cavity having lyophilized reagent disposed therein whereby the excipient reconstitutes the lyophilized reagent in situ to provide at least one calibration and/or quality control solution.

* * * * *